(12) United States Patent
Jovin et al.

(10) Patent No.: US 10,274,427 B2
(45) Date of Patent: Apr. 30, 2019

(54) EMISSION LIFETIME MEASURING METHOD AND APPARATUS FOR MEASURING A MEAN LIFETIME OF ELECTRONICALLY EXCITED STATES

(71) Applicant: MAX-PLANCK-GESELLSCHAFT ZUR FOERDERUNG DER WISSENSCHAFTEN E. V., Munich (DE)

(72) Inventors: Thomas M. Jovin, Goettingen (DE); Nathan P. Cook, Williamstown, MA (US)

(73) Assignee: Max-Planck-Gesellschaft zur Foerderung der Wissenschaften e.V., Munich (DE)

( * ) Notice: Subject to any disclaimer, the term of this patent is extended or adjusted under 35 U.S.C. 154(b) by 0 days.

(21) Appl. No.: 16/069,107

(22) PCT Filed: Jan. 13, 2016

(86) PCT No.: PCT/EP2016/000055
§ 371 (c)(1),
(2) Date: Jul. 10, 2018

(87) PCT Pub. No.: WO2017/121438
PCT Pub. Date: Jul. 20, 2017

(65) Prior Publication Data
US 2019/0003969 A1    Jan. 3, 2019

(51) Int. Cl.
*G01N 21/64* (2006.01)

(52) U.S. Cl.
CPC ..... *G01N 21/6408* (2013.01); *G01N 21/6458* (2013.01); *G01N 21/6486* (2013.01); *G01N 2021/641* (2013.01)

(58) Field of Classification Search
CPC ......... G01N 2021/641; G01N 21/6408; G01N 21/6458; G01N 21/6486
See application file for complete search history.

(56) References Cited

U.S. PATENT DOCUMENTS

| | | | | |
|---|---|---|---|---|
| 7,904,140 | B2 * | 3/2011 | Pilon | A61B 5/0059 600/476 |
| 2009/0095911 | A1 * | 4/2009 | Kim | G01N 21/6408 250/363.01 |

(Continued)

OTHER PUBLICATIONS

Becker, W., "Fluorescence Lifetime Imaging—Techniques and Applications", Journal of Microscopy, vol. 247, Pt. 2, Mar. 9, 2012, pp. 119-136.

(Continued)

*Primary Examiner* — Marcus H Taningco
(74) *Attorney, Agent, or Firm* — Caesar Rivise, PC (57) ABSTRACT

An emission lifetime measuring method, in particular for measuring a mean lifetime of electronically excited states of a sample, comprises the steps of illuminating the sample with at least one excitation light pulse, time-resolved detecting an emission response from the sample and creating a temporal detector response function, and calculating the mean lifetime of the electronically excited states on the basis of the detector response function, wherein the at least one excitation light pulse is shaped such that the sample achieves an equilibrium excited steady-state including a linearly increasing or constant number of the electronically excited states, the detector response function has a linear response function section with a constant slope, and the mean lifetime ($\tau$) of the electronically excited states is calculated on the basis of at least one of a time position of the linear response function section relative to a reference time of the at least one excitation light pulse and the slope of the linear response (Continued)

function section. Furthermore, an emission lifetime measuring apparatus (100) is described.

42 Claims, 4 Drawing Sheets

(56) References Cited

U.S. PATENT DOCUMENTS

2012/0065519 A1* 3/2012 Mincu .............. G01N 21/6408
600/476
2013/0087718 A1* 4/2013 Mei .................. G01N 21/6408
250/458.1

OTHER PUBLICATIONS

Berezin et al., "Fluorescence Lifetime Measurements and Biological Imaging", Chemical Reviews, vol. 110, No. 5, 2010, pp. 2641-2684.
De Vries et al., "Generation 3 Programmable Array Microscope (PAM) for High Speed, Large Format Optical Sectioning in Fluorescence", SPIE Proc. 9376-12, SPIE Photonics West OPTO, 2015.
Pitts et al., "Design and Developments of a Rapid Acquisition Laser-Based Fluorometer With Simultaneous Spectral and Temporal Resolution", Review of Scientific Instruments, vol. 72, No. 7, Jul. 2001, pp. 3061-3072.
Won et al., "High-Speed Confocal Fluorescence Lifetime Imaging Microscopy (FLIM) With the Analog Mean Delay (AMD) Method", Optics Express, vol. 19, No. 4, Feb. 14, 2011, pp. 3396-3404.
International Search Report for corresponding PCT Application No. PCT/EP2016/000055 dated Jul. 12, 2016.

\* cited by examiner

EMISSION LIFETIME MEASURING METHOD AND APPARATUS FOR MEASURING A MEAN LIFETIME OF ELECTRONICALLY EXCITED STATES

CROSS REFERENCE TO RELATED APPLICATIONS

This application is the U.S. National Phase Application of PCT/EP2016/000055, filed Jan. 13, 2016, the contents of which is incorporated herein by reference in its entirety for all purposes.

FIELD OF THE INVENTION

The present invention relates to an emission lifetime measuring method and apparatus, in particular for measuring a mean lifetime, e. g. a fluorescence or phosphorescence lifetime, or an equivalent feature characterizing the temporal decay of electronically excited states of a sample. Applications of the invention are available in the fields of investigating samples, e. g. in biology, medicine, material sciences or environmental technologies.

TECHNICAL BACKGROUND

The estimation of emission lifetimes (excited state lifetimes), e. g. based on fluorescence or phosphorescence emission is an essential technique in basic and applied science. Lifetime (tau, $\tau$) determinations provide sensitive measures of binding and other molecular interactions and conformational states of macromolecules, such as proteins and nucleic acids, as well as of physical properties of their microenvironment (e.g. viscosity, polarity, pH). A prominent application of time-resolved spectroscopy is FRET (Förster Resonance Energy Transfer), in which the quantum yield (and thus lifetime) of a donor fluorophore changes according to the orientation and distance (6th power dependence) of a donor molecule to an acceptor molecule.

For measuring emission lifetimes, the sample under investigation is illuminated with pulse-shaped excitation light. An emission response from the sample is detected using a detector device with time-resolution. The detector device creates a temporal detector response function (output signal function), e. g. representing the time dependency of the emission response from the sample, on the basis of which the lifetime(s) of the electronically excited states in the sample is/are calculated.

Emission lifetimes can be measured at a single sample location or with spatial resolution at a plurality of sample locations. In the latter case, an imaging modality is provided which in the case of fluorescence is called Fluorescence Lifetime Imaging (FLIM). FLIM is applied extensively in biological imaging (microscopy) in order to determine the conformation, activation, interactions and redistributions of key molecules involved in signal transduction. In biotechnology, fluorescence decay measurements are used for high-throughput screening (e.g. via binding assays) of prospective diagnostic or therapeutic molecules with designated targets.

The decay of the electronic (singlet or triplet) excited state is generally characterized by a defined probability given by the combination of various depopulation processes (in particular spontaneous emission, resonance energy transfer, non-radiative decay) and is generally exponential in nature after the cessation of the excitation source. The conventional methods for lifetime determination seek to extract the exponential time constant (reciprocal of the lifetime $\tau$), or multiple time constants in the case of heterogeneous systems, from the time course of the emissive decay curves, which are included in the measured detector response functions.

The available techniques are divided into those appropriate for discrete samples (e.g. cuvettes, microtiter plate wells) or complex specimens under the microscope. The latter case constitutes the imaging modality FLIM and requires the use of either a scanning system with one (or a few) detectors or a camera capable of acquiring a temporal sequence of 2D images. The extensive array of FLIM technologies and their comparative merits and biological applications are summarized by a large number of reviews, e.g. by W. Becker in "J. Microsc." 247: 119-136 (2012) or M. Y. Berezin et al. in "Chem. Rev." 110:2641-2684 (2010). There exist numerous related implementations of FLIM in the material sciences and other applied fields.

Scanning systems incorporated into confocal microscopes generally utilize the time-correlated single-photon counting (TCSPC) technique, which provides great inherent sensitivity and temporal resolution. Camera-based systems operating in the time domain and using a train of very narrow, excitation pulses require a gated-intensifier front-end defining programmable temporal relationships between a detection window and an excitation pulse. Similar instruments operating in the frequency domain employ periodic (sinusoidal) excitation and phase-sensitive detection. In this case, the lifetimes are derived from the modulation amplitudes and phases of the detected signals relative to that of the excitation source. Newer emerging camera systems perform phase-sensitive detection directly on the detector chip surface.

The experimental difficulty in conventional time-domain measurements, in particular FLIM, featuring excitation light pulses of narrow but finite width results from the fact that the detector response function is given by the convolution of the excitation light pulse with the exponential emissive decay function, and is thus arbitrarily complex in shape. As a consequence, short excitation light pulses (duration less to or comparable to the decay time) are required.

Furthermore, data analysis of the detector response function for deriving the decay time requires deconvolution of the response and/or restriction of the data set to a final segment of the decay. In both cases, complex mathematical procedures based on iterative minimization are involved. These require considerable computation time, even with current computers, extending to minutes in the event that more than a single decay component is present. Most FLIM applications are based on the mean decay lifetime computed from the individual decay times and their corresponding amplitudes. Deriving a mean value still requires a complete decay analysis in order to obtain the number of components and their parameters. This limitation applies to all current FLIM or single channel lifetime techniques.

OBJECTIVE OF THE INVENTION

It is an objective of the present invention to provide an improved emission lifetime measuring method and apparatus, avoiding disadvantages of conventional techniques. In particular, the method and apparatus are to be capable of measuring the emission lifetime with reduced requirements as to the duration of the excitation pulses and/or with reduced complexity of decay analysis, thus in particular facilitating FLIM measurements.

BRIEF SUMMARY OF THE INVENTION

According to a first general aspect of the invention, the above objective is solved by an emission lifetime measuring method, in particular for measuring a mean lifetime of electronically excited states of a sample, comprising the steps of illuminating the sample with at least one excitation light pulse, in particular at least two excitation light pulses, time-resolved detecting an emission response from the sample and creating a temporal detector response function, and calculating the mean lifetime of the electronically excited states on the basis of the detector response function.

Illuminating the sample comprises irradiating the sample in a solid, liquid or gaseous state with a single excitation light pulse or a sequence of identical excitation light pulses, so that the electronically excited states of the sample are obtained. The term "electronically excited states" refers to electronic states of atoms, molecules, or atom or molecule aggregates in the sample, which are excited by absorbing the at least one excitation light pulse having in particular an optical wavelength (including at least one of UV, VIS and IR wavelengths). The at least one excitation light pulse is directed to the sample in a resting or moving state in a focussed or wide-field manner. Emissive decay of the excited states along one or more electronic transitions results in a detectable emission response (rate of emission) from the sample. Depending on the composition of the sample, in particular the emission along one single electronic transition or multiple different electronic transitions, the time dependency of the emission response is determined by the single lifetime of the single electronic transition or the lifetimes of the different electronic transitions. The term "mean lifetime" refers to the single lifetime or a weighted superposition of different lifetimes (e.g. intensity mean lifetime) representing a quantitative measure of the emissive decay of a population of electronically excited states.

According to the invention, the at least one excitation light pulse has a pulse shape such that the sample achieves an equilibrium excited steady-state (also indicated as: equilibrium excited steady-state distribution) including a linearly increasing or constant number of the electronically excited states. In other words, the temporal intensity function of the pulse has at least one section with a duration which is selected such that the number of the electronically excited states of the sample is linearly growing with time or constant during the steady-state excitation section. This state of the sample is called steady-state excited state equilibrium as the numbers of absorption and emission events per time unit are balanced and the evoked emission response has a linearly growth or constant characteristic during the steady-state excitation section. In both cases of linearly increasing or constant emission response, the detector response function is created such that it includes a linear response function section (linear output signal section) with a constant positive slope.

The at least one excitation light pulse, in particular the steady-state excitation section thereof, has a duration which is longer than the emission lifetime of the sample. This is in contrast to conventional techniques wherein the lifetime is measured after an excitation of a non-equilibrium state of the sample with an ultra-short excitation pulse being substantially shorter than the lifetime to be measured. Thus, as a first main advantage of the invention, creating and controlling the at least one excitation light pulse is essentially facilitated compared with conventional techniques. A second important advantage is a greater intensity and energy of the excitation pulse, leading to an enhanced signal-to-noise characteristic of the detected emission.

Furthermore, according to the invention, the mean lifetime of the electronically excited states is calculated on the basis of a temporal position of the linear response function section relative to a reference time of the at least one excitation light pulse, e. g. begin of steady-state excitation section, and/or on the basis of the slope of the linear response function section. In particular, the mean lifetime of the electronically excited states is calculated on the basis of a temporal position of the linear response function section elicited by the least one excitation light pulse relative to the corresponding response of a reference signal representing the excitation pulse directly or the response of material with known emission decay characteristics. The linear response function section is characterized by a slope and an intercept on the temporal axis evaluated in a manner permitting a comparison with the reference response. The inventors have found, that the mean lifetime can be directly derived from the linear response function section of the detector response function. Thus, as a second main advantage of the invention, analysing the response function section is substantially facilitated. Contrary to the conventional techniques, the detector signal is analysed by linear algebraic procedures, in particular without need for a deconvolution, resulting in greatly reduced signal processing complexity. This improves in particular FLIM applications of the invention, as emission lifetime images can be measured with increased speed and/or without loss of spatial resolution in the case of an imaging system.

According to a second general aspect of the invention, the above objective is solved by an emission lifetime measuring apparatus, in particular for measuring the mean lifetime of electronically excited states of a sample, comprising an excitation source device being arranged for illuminating the sample with at least one excitation light pulse, in particular at least two excitation light pulses, a detector device being arranged for time-resolved detecting the emission response from the sample and creating the temporal detector response function, and an analysing device being arranged calculating the mean lifetime of the electronically excited states on the basis of the detector response function. According to the invention, the excitation source device is adapted for shaping the at least one excitation light pulse such that the sample achieves the equilibrium excited steady-state including the linearly increasing or constant number of the electronically excited states and the detector response function has the linear response function section with a constant slope. Furthermore, the analysing device is adapted for calculating the mean lifetime of the electronically excited states on the basis of a temporal position of the linear response function section relative to a reference time of the at least one excitation light pulse and/or on the basis of the slope and intercept of the linear response function section. Preferably, the method of the first aspect of the invention is conducted with the apparatus of the second aspect of the invention.

Advantageously, the basic concept of the invention is to replace the very narrow pulses currently used in excited state decay estimation (e.g. of fluorescence lifetime) by at least one excitation pulse encompassing a constant gradient or constant flat (plateau) section longer (e.g. 8-fold longer) than the longest excited state lifetime of the sample. The output signal of the detector device, which may include a single detector element (e. g. APDs, PMTs, hybrids, SPADs), and array of detector elements or a camera, preferably a gated intensified camera, is measured instantaneously or in integrated manner up to different, appropriately selected time points (at least 2 determinations are required). During the excited steady-state, the detector response function demonstrates a universally linear temporal increase, from which an intensity-weighted lifetime for arbitrarily complex heterogeneous solutions or microscope specimens can be instantly estimated without deconvolution, in particular without iterative techniques. The fact that very short (even sub-ns) lifetimes can be determined with long excitation light pulses is not intuitively obvious and accounts for the absence of this approach in the conventional techniques. Compared with conventional techniques, the inventive technique has advantages in terms of sensitivity of emission response detection, photon efficiency, speed of signal processing, and reduced complexity of algorithms in signal processing. Furthermore, the invention is unique in providing the mean lifetime directly, regardless of sample complexity. Furthermore, it also incorporates the capability for measurement of the individual decays without equipment modification.

According to a first embodiment of the invention, the steady-state excitation section of the at least one excitation light pulse is a linear ramp section (or: linear excitation ramp section). With a sequence of excitation light pulses, the excitation has a saw tooth intensity shape whereby the decaying limb need not be linear. The steady-state excitation section of the excitation pulse(s) has a linear increase of the pulse intensity, wherein the length the ramp is selected such that the equilibrium excited steady-state of the sample is achieved in a corresponding detection time window. During the linear ramp section, the number of electronically excited states in the sample is increasing linearly in time. Accordingly, the detector response function comprises the time-dependent emission response from the sample. The linear response function section follows the linear ramp section with a temporal delay defined by the intercept on the temporal axis defined for 0 net signal intensity or by the temporal displacement of suitably normalized signals, both cases corresponding to the mean emission lifetime to be measured.

Preferably, the mean lifetime $\tau$ of the electronically excited states is calculated with the first embodiment of the invention using the equation $\tau=t-rf(t)/srf(t)$ or an equation derived therefrom, wherein t is the time position after the initiation of the pulse, rf(t) is the emission response at the considered time position, and srf(t) is the slope of the linear response function section at time t. In the linear region, srf[t] is constant. Preferably, the mean lifetime $\tau$ is calculated with the analysing device of the lifetime measuring apparatus.

According to a second embodiment of the invention, the steady-state excitation section of the at least one excitation light pulse is a pulse section with constant intensity. The excitation light pulse is e. g. a rectangular pulse or a pulse having a flat section between curved edges. The duration of the pulse section with constant intensity is selected such that the equilibrium excited steady-state of the sample is achieved at any detection time window. During the pulse section with constant intensity, the number of electronically excited states in the sample is constant in time. Accordingly, the detector response function is created such that it comprises the time-integrated emission response from the sample. The linear response function section has a slope determined by the mean emission lifetime to be measured.

Preferably, the mean lifetime $\tau$ of the electronically excited states is calculated with the second embodiment of the invention using the equation $\tau=t-rfi(t)/srfi[t]$ or an equation derived therefrom, wherein t is a considered time position, rfi(t) is an integrated emission response at the considered time position, and srfi[t] is the slope of the linear response function section at time t. In the linear region, srfi[t] is constant. Preferably, the mean lifetime $\tau$ is calculated with the analysing device of the lifetime measuring apparatus.

Advantageously, various methods of collecting the time-integrated emission response from the sample are available. According to a first variant, the time-integrated emission response is collected with at least two integration time intervals after the start of the pulse section with constant intensity. According to a second variant, the time-integrated emission response is obtained by collecting at least one time-dependent emission response from the sample and the final value of the time-dependent emission response after the excitation pulse is finished.

According to a third embodiment of the invention, the at least one excitation light pulse includes a sequence of a segment of increasing intensity followed by a pulse section with constant intensity. The detector response function can be adapted to this more complex pulse shape by defining an effective starting time point by mathematical calculations based on the exact pulse shapes. An empirical determination is provided by determinations of the response function of a known calibration sample. The integration windows for detecting the linear response of the time-function of emission response or time-integrated emission response from the sample is collected are selected within the pulse section with constant intensity.

The duration of the steady-state excitation section of the at least one excitation light pulse is selected to be longer than the emission lifetime(s) to be measured. If the sample contains substances with known emission lifetime(s), the duration can be selected on the basis of the known data. Alternatively, in particular if the sample contains unknown substances, the duration of the steady-state excitation section can be selected on the basis of initial measurements with varying pulse shapes and selecting a pulse shape with a duration of the steady-state excitation section providing a detector response function which can be analysed with sufficient signal-to-noise ratio, precision and reproducibility.

Preferably, the linear ramp section and/or the constant pulse section of the at least one excitation light pulse have a duration, which is longer than a longest lifetime of the excited states by a factor dependent on the lifetime and the desired accuracy of the measurement. The measured lifetime using the given equations will equal the true lifetime $\tau$ multiplied by a factor=$1+\text{gamma}/(1-e^{gamma})$ where gamma=$t/\tau$. For gamma=1, 5 and 8, this factor=0.418, 0.966, and 0.997. Thus, for >99% accuracy of the calculated lifetime, the duration of the linear ramp section and/or the constant pulse section should exceed $7*\tau$ and preferably reach $10*\tau$.

It is a further advantage of the invention, that it can be used for measuring emission lifetimes in a broad time range, in particular covering fluorescence or phosphorescence events. Accordingly, the duration of the linear ramp section or the pulse section with constant intensity can be selected in a broad range from 10 ns to 10 ms. With preferred applications of the invention, the excitation source device can be adapted for an operation in certain pulse control ranges so that the duration can be at least 10 ns, in particular 50 ns; at least 100 ns, in particular 500 ns; at least 1 µs, in particular 5 µs; at least 10 µs, in particular 50 µs; at least 100 µs, in particular 500 µs; and/or at least 1 ms, in particular 5 ms.

The excitation source device preferably comprises at least one excitation light source element, like e. g. at least one LED, at least one laser diode element, and/or at least one pulsed laser source, connected with a control device providing a current control to the excitation light source element. The pulsed shaped driving current of the excitation light source element is controlled for creating the shape and duration of the at least one excitation light pulse, in particular the linear ramp section or the pulse section with constant intensity thereof. Particularly preferred, the excitation source device includes a driver circuit providing control of repetition rate, intensity, duration (width) and triggering of the at least one excitation light pulse. It is important to maintain the jitter associated with the triggering and response of the excitation source device to a value less than the desired precision of the lifetime determination, preferably <50 ps in the case of fluorescence.

According to the invention, a time position of the linear response function section relative to a reference time of the at least one excitation light pulse is used for calculating the mean lifetime of the electronically excited states and/or for estimating the slope of the linear response function section. Preferably, the reference time of the at least one excitation light pulse can be obtained from a calibration response function measured with a reference sample or a reference optical element. Accordingly, the lifetime measuring apparatus preferably includes a reference optical element being arranged for calibration purposes. In particular, an "IRF (instrument response function) cube" can be provided in the beam path of the lifetime measuring apparatus, which is constructed from linear polarizers and a quarter wave retarder and yields a reference detector signal with a "zero" lifetime from the excitation light reflected by a sample surface, e. g. a slide surface in microscope investigations. A sample with a known lifetime can also provide a calibration reference.

According to further preferred features of the invention, the emission response from the sample can be detected with a single detector element or with a plurality of detector elements, or with a time gated camera providing a mean lifetime image of the sample. The detector element/s preferably comprise/s solid-state or vacuum electronic elements and an associated detector processor providing photon counting information, in particular photon number and arrival time. The time gated camera preferably comprises a gated intensified camera with programmable gate delay and width and providing signals for synchronizing the excitation source device, preferably also providing control of pulse duration.

According to a further particularly preferred feature of the invention, the detector device is adapted for detecting the emission response from the sample with a time resolution below 50 ps, in particular below 20 ps, e. g. 10 ps or lower, and/or with a jitter below 70 ps, in particular below 50 ps, e.g. 35 ps or lower. These parameters can be obtained with time gated cameras or single detectors.

According to a particularly preferred application of the invention, the excitation source device and the detector device are integrated into a scanning microscope, in particular a microscope with super-resolution capabilities, or into a widefield microscope with optical-sectioning capabilities. Advantageously, this allows the combination of the inventive technique with available microscopy techniques, in particular for investigating biological materials.

According to a preferred variant of the invention, the detector response function can be created by detecting the emission response from the sample during a sequence of excitation pulses. In this case, the emission response is sampled with the detector device using a shifting detection or integration window. Alternatively, the detector response function can also be created by detecting the emission response from the sample with two suitably timed excitation light pulses or even only one excitation light pulse, thereby providing very high acquisition rates. The detector response function can also be created by detecting the emission response by time correlated single photon counting providing histogram of photon number and arrival time, resulting in particular advantages in terms of sensitivity, accuracy, and noise rejection.

As a further advantage of the invention, a broad range of samples can be investigated, in particular including samples with a single electronic transition which is excited by the at least one excitation light pulse, wherein the mean lifetime is the single emission lifetime of the single electronic transition, or samples with multiple electronic transitions which are excited by the at least one excitation light pulse, wherein the mean lifetime is the intensity mean emission lifetime of the electronic transitions.

Without a limitation of the invention to the following listing, examples of samples under investigation may comprise e. g. a mixture of substances, in particular macromolecules, ligands, and small molecules; probes of a microenvironment; components undergoing resonance energy transfer; a biological material, in particular a biological cell; a biological material, in particular an organelle; a pathological biological material, in particular a deposit; components distributed in an array, in particular a multiwell assay plate; a flowing stream, in particular as in a flow cytometer; entities in a channel, in particular as in a microfluidic chamber; structures of the visual system, in particular as in ophthalmology; structures of the skin, in particular as in dermatology; structures associated with teeth, in particular as in dentistry; tissues, in particular as in biopsies; tissues, in particular as in fluorescence-guided surgery; tissues, in particular as accessed by intravascular robots; autofluorescent substances, in particular as in tissues; tissues, in particular during small animal imaging; materials in forensic examinations; and/or a solid-state material, in particular a surface.

The inventive technique can be compared with conventional time-domain (e.g. TCSPC) and gated intensified camera determinations as follows. The conventional TCSCP method provides a high pulse repetition frequency (e.g. >40 MHz), but a much lower acquisition rate (e.g. 1%) due to requirement for single photon detection without "pileup", thus also limiting the method to low level signals. Furthermore, it has low excitation duty cycles in point scanning (confocal) systems, and the signal analysis generally requires iterative curve fitting. The conventional gated intensified camera FLIM with narrow pulses has a low emission detection efficiency due to need for narrow gate windows, successively displaced in time to define the decay curve, a low signal intensity due to use of narrow, low energy excitation pulses, and the signal analysis requires iterative curve fitting. The conventional method can also be configured with a small number of detections windows with variable duration but is unable to provide reliable lifetimes of complex mixtures and is limited in sensitivity due to the use of narrow excitation pulses.

On the contrary, the invention provides efficient excitation with simple high intensity, high energy "long" pulses, applicability for all signal levels (very low to very high, single or multi-photon), simple nature of the detector response function signals, and applicability with mean lifetimes regardless of sample heterogeneity. Estimating the mean lifetime simple is provided with a non-iterative analysis with immediate readout, and the invention can be applied in all time domains (ps to s). Additional measurements modes such as direct decay curve analysis can also be accommodated by the same instrument. The invention provided a very high acquisition speed (2 appropriately selected gate widths suffice), which is unachievable with present commercial system, and a high sensitivity in particular due to the intensifier and emCCD detector incorporated in commercially available cameras. Furthermore, the mean emission lifetime can be obtained by a conventional point-by-point decay analysis but with much higher signal levels than in the case of the conventional FLIM systems. Finally, the lifetime measuring apparatus has advantages in terms of lowest system cost and complexity.

BRIEF DESCRIPTION OF THE DRAWINGS

Further details and advantages of the invention are described in the following with reference to the attached drawings, which show in.

DETAILED DESCRIPTION OF PREFERRED EMBODIMENTS

The invention is described in the following with exemplary reference to the first and second embodiments using the at least one excitation light pulse with a linear ramp section or a pulse section with constant intensity. The invention is not restricted to these embodiments, but rather can be implemented with variants of the third embodiment including combinations of the linear ramp section and pulse section with constant intensity. Furthermore, exemplary reference is made to an application of the invention, wherein at least the detector device is integrated into a microscope with a camera detector. The invention is not restricted to this application, but rather can be implemented in a corresponding manner with a scanning microscope or an optical setup without imaging modality, like in a conventional lifetime measurement.

Embodiments of Emission Lifetime Measuring Apparatus

Figure 1:
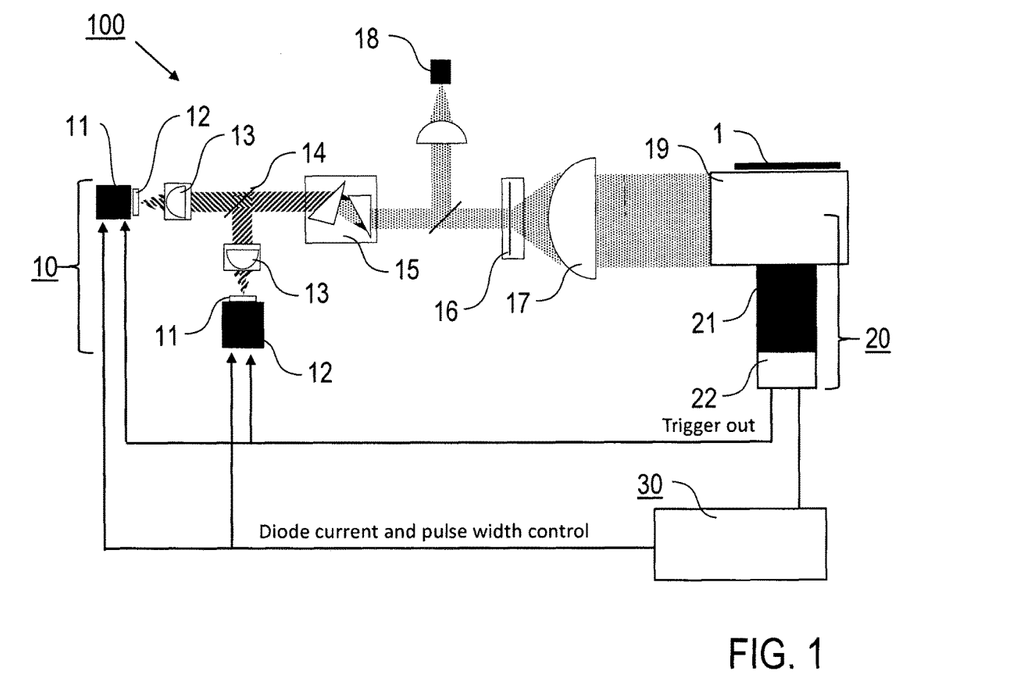
FIG. 1: a schematic representation of a preferred embodiment of the emission lifetime measuring apparatus according to the invention.

FIG. 1 schematically illustrates a preferred embodiment of the emission lifetime measuring apparatus 100 according to the invention, including an excitation source device 10, a detector device 20 and an analysing device 30.

The excitation source device 10 comprises two laser diodes 11 each with a driver circuit 12 allowing control of pulse current, width, and shape, and with a collimation optic 13. The laser diodes 11 (manufacturer: e. g. OSRAM, e. g. model TB450B) emit at different wavelengths, e. g. selected from 405 nm, 450 nm, 520 nm and 661 nm. The driver circuits 12 (manufacturer: e. g. PICOLas, Highland Technologies, or Thorlabs) are connected with a detector processor 22 of the detector device 20. The collimated outputs of the laser diodes 11 are combined with a dichroic mirror 14 to a common beam path, which is directed via a circularizer 15 (shown rotated 90°) and laser speckle reducer and diffuser 16 (manufacturer: Optotune) and an aspheric condenser 17 to a sample 1 in a microscope 19, e. g. Olympus IX71, including objectives and filters (not shown in details). The output of the laser diode 11 currently in operation is optically monitored with a fast photodiode pulse monitor 18 (manufacturer: New Focus, e.g. model 1621), receiving a portion of the laser diode output via an uncoated beam splitter and a focussing optic. The output of this detector is monitored by an oscilloscope (not shown). According to alternative embodiments of the invention, the emission lifetime measuring apparatus 100 can be provided with a single laser diode or more than two laser diodes or at least one other source element, like a LED or a pulsed laser.

Advantageously, the laser diodes are more versatile and much cheaper than commercial systems based on femtosecond lasers or laser diodes configured for generating very narrow (10-1000) ps signals. Furthermore, the achievable pulse energies in the inventive apparatus are 1-2 orders of magnitude greater, leading to greatly reduced photon noise and increased image quality.

The output of the laser diode 11 preferably is coupled to the microscope 19 by employing a PAM setup (Programmable Array Microscopy setup, not shown in detail). The PAM setup, which is described in detail in de Vries et al. in "SPIE Proc." 9376-12, 2015, includes a programmable micro-mirror array (Texas Instruments digital mirror device, DMD) to generate systematic patterns of excitation and correlated detection in fluorescence microscopy. The system is very rapid and sensitive in the generation of large format, optically sectioned images of living and fixed cells and tissues. All emission parameters (intensity, spectrum, polarization, lifetime) can be employed.

The microscope 19 is provided with the detector device 20 comprising a gated intensified camera 21 which is coupled to a side port of the microscope 19, and the integrated detector processor 22. The gated intensified camera 21 preferably has a Gen-III intensifier and an optimized dual gain mechanism; a gate width down to 0.5 ns; a high gating repetition rate (up to 1 MHz) with on-CCD accumulation; and/or an emCCD detector with negligible readout noise. Further advantageous features of the gated intensified camera 21 are high linearity, photon counting capability, and a large 1K×1K format; versatile electronics and software for configuring acquisition and readout, including synchronization of the pulsed excitation source device 10; and a timing resolution of 10 ps and timing jitter of 35 ps. Precise signal integration is an inherent feature of gated intensified camera 21, in particular with tight control of gate width and position.

A first output of the detector processor 22, e. g. an auxiliary output of the PI-MAX4 timing unit, is coupled with the driver circuits 12, while a second output of the detector processor 22 is coupled with the analysing device 30. Via the first output, a trigger and pulse width control signal is submitted to the driver circuits 12, controlling the time position and pulse width of the excitation light pulses for irradiating the sample 1. Via the second output, a detector response function is submitted to the analysing device 30 for calculating the mean lifetime of the sample 1. Furthermore, the analysing device 30 is configured for providing a diode current control of the laser diodes 11.

The analysing device 30 comprises a computer circuitry, running in particular control software, like LightField operation control software, and being coupled with a timing generator, like the SuperSynchro timing generator integrated into the camera 21. Complex schemes involving automated successive increments of pulse width and/or delay can be implemented with the detector timing circuitry and processor 22.

The gated intensified camera 21 is e. g. the PI-MAX4 1024EMD camera (manufacturer: Princeton Instruments). The PI-MAX4 camera provides advantages in particular in terms of number of collected frames per second (in a range of 10 to 300, with a 10 MHz digitization) and acquisition time (in a range of 7 to 230 ms with 2 frames with no averaging, 65-2300 ms with 2 frames and 10 repeats, or 3 to 115 sec with 200 frames and 5 repeats). Furthermore, the PIMAX-4 also features a double image feature allowing the camera to take a two frames with a delay of ~450 ns (phosphor decay time limited).

However, the invention is not restricted to the PI-MAX4 camera but can be implemented with other gated, intensified cameras as well as detectors comprising a single or a few (<100) elements.

Embodiments of Emission Lifetime Measuring Method

For conducting the emission lifetime measuring method of the invention, the sample 1 in microscope 19 is irradiated with at least one excitation light pulse from the excitation source device 10. An emission response, e. g. a fluorescence response, from sample 1 is detected with temporal resolution. Time resolved detection is obtained with a single excitation pulse or with a sampled sequence of excitation pulses, e. g. with a repetition rate of up to 1 MHz. Depending on the gate width of the camera 21, the collected temporal detector response function comprises a time-dependent emission response or an integrated time-dependent emission response from sample 1. On the basis of the collected temporal detector response function, the mean lifetime of the electronically excited states of sample 1 is calculated as outlined in the following.

The lifetime of the excited state can be interpreted as the mean arrival time of emission photons after a delta pulse excitation. That is, the lifetime constitutes a delay between the excitation and emission signals. The inventors have found that this delay not only can be measured after a delta pulse excitation, but also in an equilibrium excited steady-state of sample 1 with a linearly increasing or constant number of the electronically excited states. This circumstance, i.e. the direct measurement of this delay, forms the basis of the inventive emission lifetime measuring method.

Preferably, the excitation light pulse has a linear ramp section 2 (first embodiment of the invention, see FIG. 3) or a pulse section 3 with constant intensity (second embodiment of the invention, see FIG. 4), creating the equilibrium excited steady-state of sample 1 and the detector response function having a linear response function section with a constant slope as described in the following.

Figure 3:
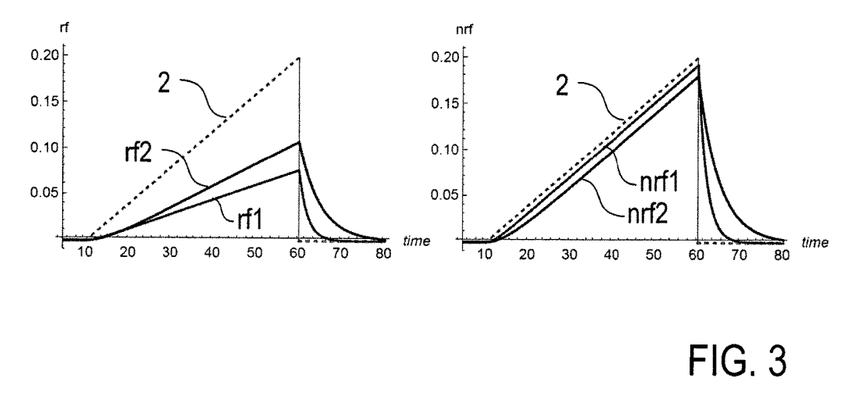
FIGS. 3 and 4: excitation and response curves illustrating embodiments of the emission lifetime measuring apparatus according to the invention

According to FIG. 3, the dotted line represents the ramp section 2 of an excitation light pulse according to the first embodiment of the invention. In the equilibrium excited steady-state of sample 1, the time-dependent emission response rf of the sample has a linear response function section (linearly increasing ramp shape) as well. Drawn lines rf1 and rf2 in FIG. 3A illustrate two examples of samples having a fluorescence lifetime of 2 ns (rf1) and 5 ns (rf2). Due to the longer fluorescence lifetime, the linear response function section of emission response rf2 has a steeper slope and a higher final value than the linear response function section of emission response rf1. Emission responses rf1 and rf2 are displaced relative to the excitation light pulse and relative to each other. The displacement, which is further demonstrated with the normalized detector response function in FIG. 3B, is linearly dependent on the mean lifetime of the sample, being equal to the lifetime upon comparison with a reference sample with a 0 or known finite lifetime.

The response function curves immediately after the initial rise and final fall of the excitation light pulse 2 are exponential and provide additional data for obtaining the lifetimes according to conventional techniques.

Estimating the mean lifetime on the basis of at least one of a time position of the linear response function section relative to a reference time of the at least one excitation light pulse and the slope of the linear response function section is conducted with a practical example of the first embodiment as follows (time units: ns). The excitation light pulse (ramp pulse) starts at t1=10 and ends at 60. The linear response function section (ca. 8τ to 10τ) of rf corresponds to t≈50 to 60.

| | |
|---|---|
| rfIRF[t] = (t − t1) · sIRF | nrf1 = rf1 · sIRF/s1 |
| s1 = slope of rf1 = 0.0016 | nrf2 = rf2 · sIRF/s2 |
| s2 = slope of rf2 = 0.0024 | |
| sIRF = slope of rfIRF = 0.004 | |

(IRF: instrument response function, i.e. emission response with τ = 0, corresponding to ramp section 2 of the excitation light pulse)

The analysis method only requires rf data, and in principle, only 2 points in the linear response function section. For plotting (but not needed for lifetime calculation), one normalizes the emission response curves by dividing the ratio of their slopes s1 and s2 (in the linear response function section) to that of the irf curve (sIRF), leading to FIG. 3B.

The lifetimes are given by the horizontal displacements in the linear response function section.

Now, nrf1 at a given t is equal to rfIRF at a corresponding tIRF; the same applies to nr1

This leads to:

τ=t−tIRF=t−t1 −rf[t]/s (by cancellation, one only need the original rf values and their slopes in the linear region). Experimentally, t1 is determined from the IRF curve:

t1=t−rfIRF[t]/sIRF

For example at t=55, rf1=0.0688 and rf2=0.096

τ1=55−10−0.0688/0.0016=2 ns and

τ2=55−10−0.96/0.0024=5 ns

It is thus confirmed that the input values for the lifetimes in this example are reproduced With the first embodiment of the invention, the recorded signals (and thus the achievable SNR) are necessarily lower than with the second embodiment (see below) because point-by-point measurements using narrow gate widths must be made. Nonetheless, a higher (e.g. 3×) signal level compared to that with conventional narrow pulse excitation is still feasible.

According to FIG. 4A, the dotted line represents the pulse section 3 with constant intensity of an excitation light pulse according to the second embodiment of the invention. The extended rectangular excitation light pulse 3 provides a rapid increase in excitation energy followed by a constant level which is maintained for an interval corresponding to several times the lifetime(s) being measured. The response function curves immediately after the initial rise and final fall of the excitation light pulse 3 are exponential and provide additional data for obtaining the lifetimes according to conventional techniques.

Drawn lines rf1 and rf2 in FIG. 4A illustrate two examples of samples having a fluorescence lifetime of 2 ns (rf1) and 5 ns (rf2). In the equilibrium excited steady-state of sample 1, the time-dependent emission response rf of the sample has a flat shape (FIG. 4A), while the time-integrated emission responses rfi1, rfi2 of the samples which are actually recorded n the experiment each have a linear response function section (linearly increasing ramp shape in dependency on the integration time or gate width, FIG. 4B). A linear variation with integration time (detection gate width of the detector device, e. g. camera 21) after achieving the steady-state, and a separation on the time axis in this linear region corresponding exactly to the difference in lifetime (e. g. 3 ns for the 2 and 5 ns signals) are obtained.

The origin of the linear rfi response can be derived from the following mathematical calculation. The response to a step (or rectangular) excitation is an exponentially increasing function, $\tau \cdot (1-\mathrm{Exp}[-t/\tau])$. The integral of this signal is given by $\tau \cdot [t-\tau \cdot (1-\mathrm{Exp}[-t/\tau])]$, which for $t \gg \tau$ reduces to $\tau[t-\tau]$, a linear function in t reflecting the attainment of the steady-state excited state equilibrium. The amplitude (slope) of this linear response varies with $\tau$ (as well as with probe concentration and spectroscopic properties, and various instrument parameters), while the position of the linear region is displaced on the time (gate width) axis by a value equal to $\tau$, i.e. the delay arising from the stochastic nature of emission and alluded to earlier.

All rfi responses normalized by their respective end (plateau) values, i.e. after cessation of the excitation pulse, demonstrate the same linear response regardless of the number of components varying in $\tau$ and amplitude, as shown in FIG. 4C. The universal, constant slope of the normalized integrated response functions is dictated uniquely by the pulse parameters (for the rectangular pulse in FIG. 4A, the slope=1/pulse width) and the temporal displacements correspond to the mean $\tau$ values (or their differences). These displacements can also be computed by extrapolation of the non-normalized rfi to the time axis corresponding to 0 signal intensity. Computation of absolute lifetimes is facilitated by integrating a reference optical element 23 to the optical setup, like an "IRF (instrument response function) cube", constructed from linear polarizers and a quarter wave retarder and integrated in the microscope 19 of the experimental eeFLIM system (FIG. 1). The reference optical element yields a reference signal with a "zero" lifetime from the excitation light reflected by the sample slide surface. A sample with known lifetime can also provide a calibration reference.

Figure 2:
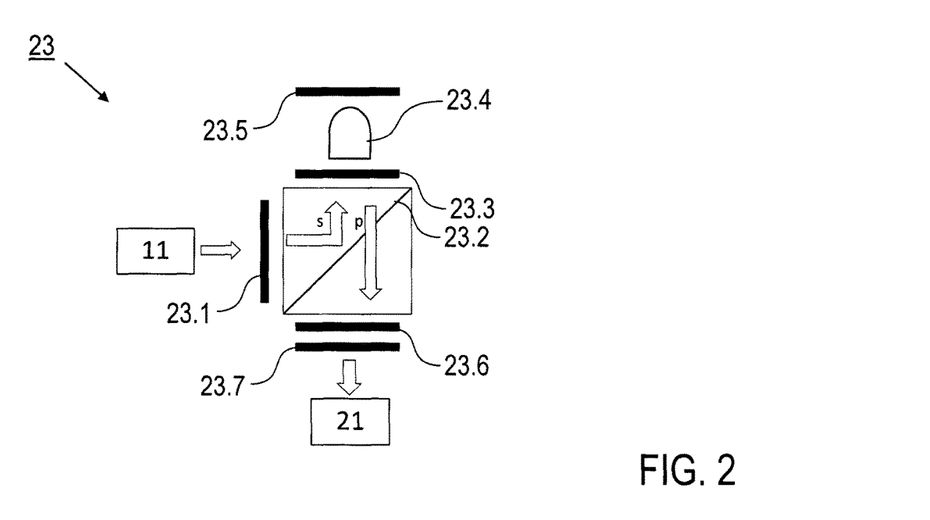
FIG. 2: a schematic representation of a reference optical element included in the emission lifetime measuring apparatus of FIG. 1.

An example of the reference optical element 23, is illustrated in FIG. 2. The reference optical element 23 comprises a linear s polarizer 23.1, a broadband beam splitter 23.2 (e.g. 80% T, 20% R), a quarter wave plate 23.3, the microscope objective 23.4, a mirror 23.5 on the microscope stage, a linear p polarizer 23.6, and a neutral density filter 23.7. A portion reflected at the mirror 23.5 provides a stable reference signal ("0" lifetime), in particular for absolute lifetime measurements.

Normalization (using the final signal value) is not strictly necessary inasmuch as 2 points allow a determination of the slope. Its value relative to that of the normalized reference signal (IRF) can be used to adjust the signal values so as to be compatible with those of the reference, allowing the calculation of the temporal "displacements" equal to the lifetimes.

Figure 4:
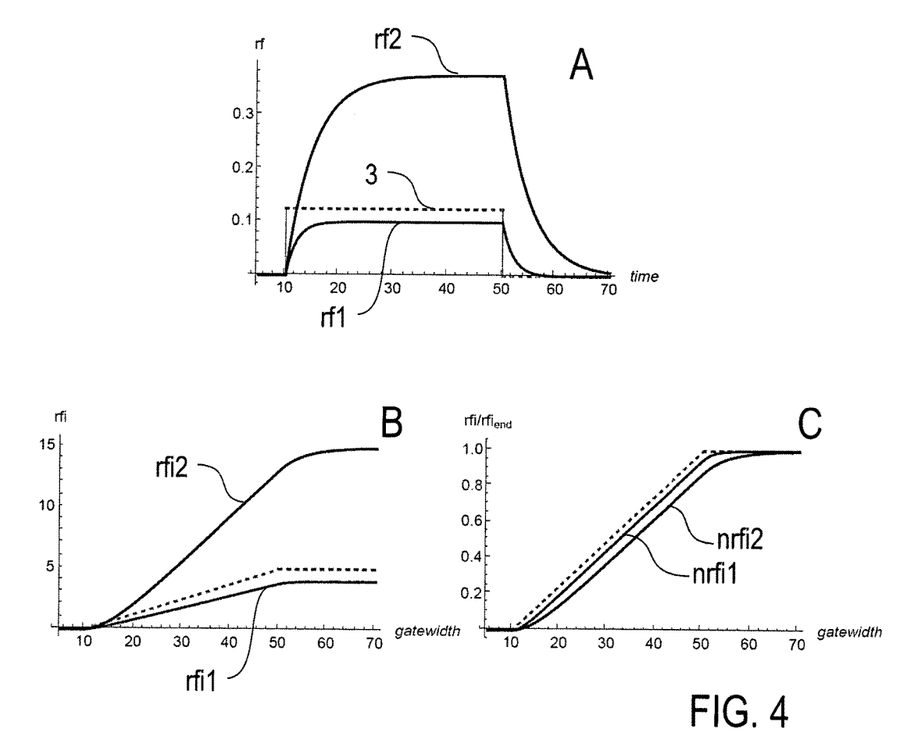

Estimating the mean lifetime on the basis of at least one of a time position of the linear response function section relative to a reference time of the at least one excitation light pulse and the slope of the linear response function section is conducted with a practical example of the second embodiment as follows.

The rectangular pulse starts at t1=10 and ends at 50. The linear response function section (ca. $6\tau$ to $8\tau$) of rf corresponds to t$\simeq$40 to 50.

| | |
|---|---|
| fr = final rfi1 = 4 (=amp1 · $\tau$1) | nrfi1 = rfi1/fr |
| fb = final rfi2 = 15 (=amp2 · $\tau$2) | nrfi2 = rfi2/fb |
| firf = final rfiIRF = 5 (=ampIRF) | nrfiIRF = rfiIRF/firf |
| s1 = slope rfi1 = 0.1 (=rf1, max) | nsIRF = sIRF/firf |
| | (normalized slope of rfiIRF) |
| s2 = slope rfi2 = 0.375 (=rf2, max) | |
| sIRF = slope rfi IRF = 0.125 (=rfIRF, max) | |

The analysis method only requires rfi data, and in principle, only 2 points, one in the linear linear response function section and one at the end of the final decay). One normalizes the rf data in the linear region by division by the respective final rfi values, as shown in FIG. 4C. The slopes of rf are now all equal.

For every nrf1 or nrf1 point (at their respective times t) there is a corresponding value of nirf with its value of tIRF (<t). Thus, nrfi1 at a given t=nrfiIRF at a corresponding tIRF; the same applies to nrfi2

$$\tau = t - tIRF = t - t1 - nrf[t]/nsIRF$$

For example at t=45, nrf1=0.825 and nrf2=0.75. n sIRF=0.025

$$\tau 1 = 45 - 10 - 0.825/0.025 = 2 \text{ ns},$$

and $$\tau 2 = 40 - 10 - 0.75/0.025 = 5 \text{ ns}$$

Pulse shapes other than rectangular, i.e. with different shapes (finite rise times), can also be used in the invention (third embodiment). The response curves and the analytical mathematical expressions for the corresponding rfi curves have been computed for numerous examples. In all cases, the same behaviour of the rfi signals is observed after attainment of the steady state, i.e. as in FIG. 4B for the rectangular pulse.

With a practical measurement according to the second embodiment (using the pulse section 3 with constant intensity), the integration is started before the excitation light pulse 3, then keep incrementing the gate width (always starting from the same point) until the excitation is completed (end of the excitation light pulse). With 100-200 points (frames) one defines the integrated response function in detail. In the case of the rectangular excitation light pulse 3, the immediate "dynamic response" (population kinetics of the excited state) takes place on a time scale dictated by the lifetime. 'After a few lifetimes have passed, the system achieves the steady-state defined by the combination of the constant excitation rate (irradiance*absorption cross-section) and the decay rate (inverse excited state lifetime). The rate of emission is constant since the irradiance is constant, thus leading to a linearly increasing integrated response as time progresses. When the pulse ends ("runs out"), the system decays as it would do "normally" when using delta function excitation. In theory (and practice) two points acquired in the linear response function section suffice for determining the lifetime.

Figure 5:
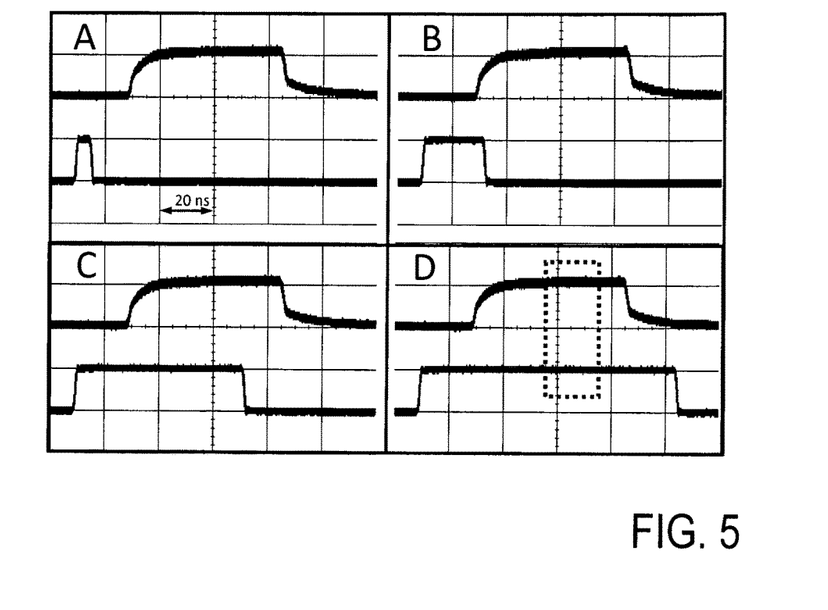
FIG. 5: time functions of excitation source and detector functions illustrating signal acquisition using a rectangular excitation pulse.

FIG. 5 illustrates the image acquisition using a rectangular excitation light pulse. The upper trace in each panel A to D shows the signal of the photodiode 18 monitoring the excitation light pulses. The lower trace illustrates the intensifier gate (monitor output from the camera 21). FIG. 5A shows the start of image acquisition. The intensifier gate extends into excitation light pulse (FIG. 5B) and migrates through laser pulse (FIG. 5C), until it encompasses the entire excitation light pulse (FIG. 5D). The enclosed area is a region of constant illumination intensity.

Figure 6:
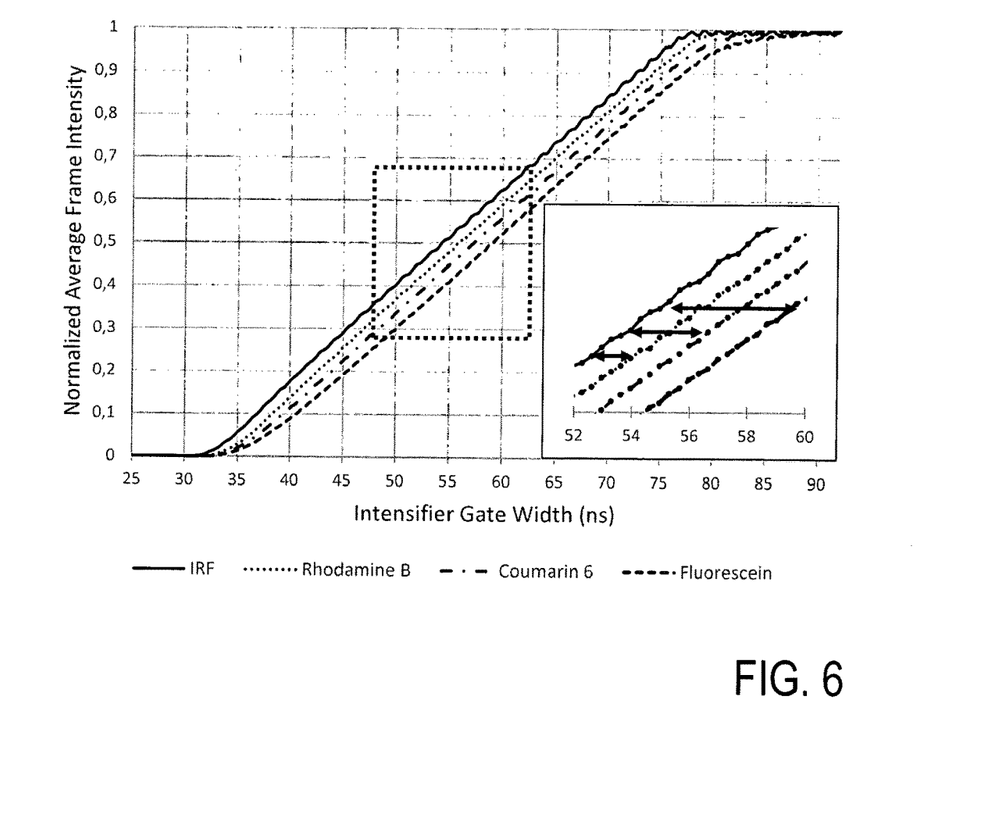
FIGS. 6 and 7: experimental results obtained with the inventive technique.

Processed integrated response functions are illustrated in FIG. 6, which shows mean normalized rfi signals from IRF and three fluorescence dye solutions. The rfi signal from IRF is obtained from excitation light reflected from the microscope focal plane. The fluorescence lifetime is given by the displacement of the parallel linear response function sections corresponding to the period of constant illumination (enclosed area; see also FIG. 4). The inset highlights the horizontal (temporal) displacements (equal to the lifetimes) of the measured dyes Rhodamine B (1.6 ns), Coumarin 6 (2.5 ns), and dianionic Fluorescein (4.1 ns).

Figure 7:
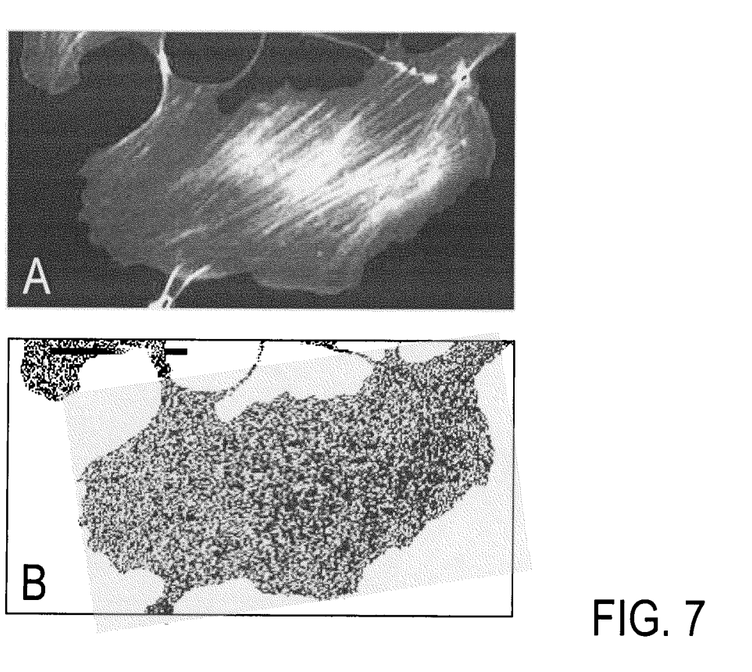

FIG. 7 shows examples of microscopy images of 3T3 cells stained for their actin cytoskeleton with bodipyFL-phallacidin. FIG. 7A depicts the total integrated rfi signal of the last acquired frame (longest of 200 gate width increments, each 0.3 ns), and FIG. 7B shows the image of $\tau$ values.

The features of the invention in the above description, the drawings and the claims can be of significance both individually as well in combination or sub-combination for the realization of the invention in its various embodiments.

The invention claimed is:

1. An emission lifetime measuring method for measuring a mean lifetime of electronically excited states of a sample, comprising:
    illuminating the sample with at least one excitation light pulse;
    time-resolved detecting an emission response from the sample and creating a temporal detector response function; and
    calculating the mean lifetime of the electronically excited states on the basis of the detector response function, wherein
    the at least one excitation light pulse is shaped such that the sample achieves an equilibrium excited steady-state including a linearly increasing or constant number of the electronically excited states,
    the detector response function has a linear response function section with a constant slope, and
    the mean lifetime ($\tau$) of the electronically excited states is calculated on the basis of at least one of a time position of the linear response function section relative to a reference time of the at least one excitation light pulse and the slope of the linear response function section.

2. The emission lifetime measuring method according to claim 1, wherein
    the at least one excitation light pulse includes a linear ramp section, and
    the detector response function includes the time-dependent emission response from the sample including the linear response function section.

3. The emission lifetime measuring method according to claim 2, wherein the mean lifetime ($\tau$) of the electronically excited states is calculated on the basis of $\tau=t-rf(t)/srf(t)$, wherein t is the time position after the initiation of the pulse, rf(t) is the emission response at the considered time position, and srf(t) is the slope of the linear response function section at time t.

4. The emission lifetime measuring method according to claim 1, wherein
    the at least one excitation light pulse includes a pulse section with constant intensity, and
    the detector response function comprises the time-integrated emission response from the sample including the linear response function section.

5. The emission lifetime measuring method according to claim 4, wherein the mean lifetime ($\tau$) of the electronically excited states is calculated on the basis of $\tau=t-rfi(t)/srfi(t)$, wherein t is a considered time position, rfi(t) is an integrated emission response at the considered time position, and srfi(t) is the slope of the linear response function section at time t.

6. The emission lifetime measuring method according to claim 4, wherein the time-integrated emission response from the sample is collected with at least two integration time intervals after the start of the pulse section with constant intensity.

7. The emission lifetime measuring method according to claim 4, wherein the time-integrated emission response from the sample is obtained by collecting at least one time-dependent emission response from the sample and the final invariant value of the time-dependent emission response.

8. The emission lifetime measuring method according to claim 2, wherein the at least one excitation light pulse includes the linear ramp section or the pulse section with constant intensity having a duration, which is longer than a longest lifetime of the excited states of the sample by a factor of at least one of at least 5 and at most 12.

9. The emission lifetime measuring method according to claim 2, wherein the at least one excitation light pulse includes the linear ramp section or the pulse section with constant intensity having a duration, which is longer than a longest lifetime of the excited states of the sample by a factor of at least one of at least 7 and at most 10.

10. The emission lifetime measuring method according to claim 8, wherein the duration of at least of the linear ramp section and the pulse section with constant intensity is selected in a range from 10 ns to 10 ms.

11. The emission lifetime measuring method according to claim 1, wherein the mean lifetime ($\tau$) is calculated using a calibration response function obtained from a reference sample or a reference optical element.

12. The emission lifetime measuring method according to claim 1, wherein the emission response from the sample is detected with a single detector element or with an array of detector elements.

13. The emission lifetime measuring method according to claim 1, wherein the emission response from the sample is detected with a time gated camera providing a mean lifetime image of the sample.

14. The emission lifetime measuring method according to claim 1, wherein
    the sample includes a single electronic transition which is excited by the at least one excitation light pulse, and
    the mean lifetime ($\tau$) is the single emission lifetime of the single electronic transition.

15. The emission lifetime measuring method according to claim 1, wherein
    the sample includes multiple electronic transitions which are excited by the at least one excitation light pulse, and
    the mean lifetime ($\tau$) is the intensity mean emission lifetime of the electronic transitions.

16. The emission lifetime measuring method according to claim 1, wherein the detector response function is created by detecting the emission response from the sample during one single excitation pulse.

17. The emission lifetime measuring method according to claim 1, wherein the detector response function is created by detecting the emission response from the sample during a sequence of excitation pulses.

18. The emission lifetime measuring method according to claim 1, wherein the detector response function is created by detecting the emission response with time correlated single photon counting.

19. The emission lifetime measuring method according to claim 1, wherein the sample includes at least one of:
a mixture of substances,
macromolecules,
ligands,
small molecules,
probes of a microenvironment,
components undergoing resonance energy transfer,
a biological material,
a biological cell,
a biological organelle,
a pathological biological material,
a pathological biological deposit,
components distributed in an array,
components distributed in a multiwell assay plate,
a flowing stream,
a flowing stream in a flow cytometer,
entities in a channel,
entities in a microfluidic chamber,
structures of the visual system,
structures of the visual system as in ophthalmology,
structures of the skin,
structures of the skin as in dermatology,
structures associated with teeth,
structures associated with teeth as in dentistry,
tissues,
tissues as in biopsies,
tissues as in fluorescence-guided surgery,
tissues as accessed by intravascular robots,
autofluorescent substances,
autofluorescent substances as in tissues,
tissues during small animal imaging,
materials in forensic examinations,
a solid-state material, and
a solid-state material surface.

20. An emission lifetime measuring apparatus, for measuring a mean lifetime ($\tau$) of electronically excited states of a sample, comprising:
an excitation source device being arranged for illuminating the sample with at least one excitation light pulse;
a detector device being arranged for time-resolved detecting an emission response from the sample and creating a temporal detector response function; and
an analysing device being arranged calculating the mean lifetime ($\tau$) of the electronically excited states on the basis of the detector response function, wherein
the excitation source device is configured to shape the at least one excitation light pulse such that the sample achieves an equilibrium excited steady-state including a linearly increasing or constant number of the electronically excited states and the detector response function has a linear response function section with a constant slope, and
the analysing device is configured to calculate the mean lifetime ($\tau$) of the electronically excited states on the basis of at least one of a time position of the linear response function section relative to a reference time of the at least one excitation light pulse and the slope of the linear response function section.

21. The emission lifetime measuring apparatus according to claim 20, wherein
the excitation source device is configured to create the at least one excitation light pulse having a linear ramp section, and
the detector device is configured to create the temporal detector response function having the time-dependent emission response from the sample including the linear response function section.

22. The emission lifetime measuring apparatus according to claim 21, wherein the analysing device being is configured to calculate the mean lifetime ($\tau$) of the electronically excited states on the basis of $\tau=t-t_s-rf(t)/s$, wherein t is a considered time position, $t_s$ is a reference start time of the linear ramp section, rf(t) is the emission response at the considered time position, and s is the slope of the linear response function section.

23. The emission lifetime measuring apparatus according to claim 20, wherein
the excitation source device is configured to create the at least one excitation light pulse having a pulse section with constant intensity, and
the detector device is configured to create the temporal detector response function having the time-integrated emission response from the sample including the linear response function section.

24. The emission lifetime measuring apparatus according to claim 23, wherein the analysing device being is configured to calculate the mean lifetime ($\tau$) of the electronically excited states is calculated on the basis of $\tau=t-t_s-rfi(t)/s$, wherein t is a considered time position, $t_s$ is a reference start time of the constant pulse section, rfi(t) is an integrated emission response at the considered time position, and s is the slope of the linear response function section.

25. The emission lifetime measuring apparatus according to claim 23, wherein the detector device is configured to collect the time-integrated emission response from the sample with at least two integration time intervals after the start of the pulse section with constant intensity.

26. The emission lifetime measuring apparatus according to claim 23, wherein the detector device is configured to collect at least one time-dependent emission response from the sample and the final value of the time-dependent emission response achieved after termination of the excitation light pulse.

27. The emission lifetime measuring apparatus according to claim 21, wherein the excitation source device is configured to create the at least one excitation light pulse such that it includes the linear ramp section or the pulse section with constant intensity having a duration, which is longer than a longest lifetime of the excited states of the sample by a factor of at least of at least 5 and at most 12.

28. The emission lifetime measuring apparatus according to claim 21, wherein the excitation source device is configured to create the at least one excitation light pulse such that the duration of the linear ramp section or the pulse section with constant intensity is selected in a range from 10 ns to 10 ms.

29. The emission lifetime measuring apparatus according to claim 20, wherein the excitation source device includes at least one of a laser diode, an LED, and a pulsed laser.

30. The emission lifetime measuring apparatus according to claim 20, wherein the excitation source device includes driver circuit providing at least one of a repetition rate, intensity, triggering and gate width control.

31. The emission lifetime measuring apparatus according to claim 20, further comprising a reference optical element being arranged for calibration purposes.

32. The emission lifetime measuring apparatus according to claim 20, wherein the detector device includes one of a single detector element, an array of detector elements, and a time gated camera providing a mean lifetime image of the sample.

33. The emission lifetime measuring apparatus according to claim 32, wherein the detector device includes a single or multiple solid-state or vacuum electronic elements and an associated detector processor providing photon counting information.

34. The emission lifetime measuring apparatus according to claim 32, wherein the detector device includes a single or multiple solid-state or vacuum electronic elements and an associated detector processor providing photon number and arrival time.

35. The emission lifetime measuring apparatus according to claim 32, wherein the detector device includes a gated intensified camera with programmable gate delay and width and providing signals for synchronizing the excitation source device.

36. The emission lifetime measuring apparatus according to claim 20, wherein the detector device is configured to create the detector response function by detecting the emission response from the sample during one single excitation pulse.

37. The emission lifetime measuring apparatus according to claim 20, wherein the detector device is configured to create the detector response function by detecting the emission response from the sample during a sequence of excitation pulses.

38. The emission lifetime measuring apparatus according to claim 20, wherein the detector device is configured for time correlated single photon counting.

39. The emission lifetime measuring apparatus according to claim 20, wherein the detector device is configured to detect the emission response from the sample with at least of a time resolution below 50 ps and a jitter below 70 ps.

40. The emission lifetime measuring apparatus according to claim 20, wherein the excitation source device and the detector device are integrated into a microscope.

41. The emission lifetime measuring apparatus according to claim 40, wherein the excitation source device and the detector device are integrated into a scanning microscope with super-resolution capabilities.

42. The emission lifetime measuring apparatus according to claim 40, wherein the excitation source device and the detector device are integrated into a wide-field microscope with optical-sectioning capabilities.

* * * * *